(12) United States Patent
Kuboe et al.

(10) Patent No.: US 7,951,851 B2
(45) Date of Patent: May 31, 2011

(54) CURABLE COMPOSITION FOR DENTAL PURPOSES

(75) Inventors: Yoshiko Kuboe, Kurashiki (JP); Takahiro Sekiguchi, Kurashiki (JP)

(73) Assignee: Kuraray Medical Inc., Kurashiki-shi (JP)

( * ) Notice: Subject to any disclaimer, the term of this patent is extended or adjusted under 35 U.S.C. 154(b) by 124 days.

(21) Appl. No.: 12/525,323

(22) PCT Filed: Jan. 24, 2008

(86) PCT No.: PCT/JP2008/051003
§ 371 (c)(1),
(2), (4) Date: Jul. 31, 2009

(87) PCT Pub. No.: WO2008/093596
PCT Pub. Date: Aug. 7, 2008

(65) Prior Publication Data
US 2010/0105802 A1 Apr. 29, 2010

(30) Foreign Application Priority Data
Feb. 1, 2007 (JP) .................................. 2007-023538

(51) Int. Cl.
*C08F 2/46* (2006.01)
*C08J 3/28* (2006.01)
(52) U.S. Cl. ......... 523/116; 523/115; 523/117; 523/200
(58) Field of Classification Search ........... 523/36 –118, 523/200, 213, 492; 428/447; 252/51–520.2; 524/379–588; 260/1
See application file for complete search history.

(56) References Cited

U.S. PATENT DOCUMENTS

| | | | | |
|---|---|---|---|---|
| 3,324,074 | A * | 6/1967 | McManimie | 526/279 |
| 3,427,337 | A * | 2/1969 | Miller et al. | 556/440 |
| 3,442,851 | A * | 5/1969 | McManimie | 524/492 |
| 5,192,815 | A * | 3/1993 | Okada et al. | 523/115 |
| 6,756,124 | B2 * | 6/2004 | Kanamori et al. | 428/447 |
| 6,933,327 | B2 * | 8/2005 | Yamakawa et al. | 523/115 |
| 2003/0036582 | A1 * | 2/2003 | Yamakawa et al. | 523/115 |
| 2003/0162863 | A1 * | 8/2003 | Satoh et al. | 523/109 |
| 2010/0105802 | A1 * | 4/2010 | Kuboe et al. | 523/116 |

FOREIGN PATENT DOCUMENTS

| | | | |
|---|---|---|---|
| EP | 368657 | * | 5/1990 |
| JP | 2-134307 | | 5/1990 |
| JP | 3-70778 | | 3/1991 |
| JP | 11-335220 | | 12/1999 |
| JP | 2002-255721 | | 9/2002 |
| WO | WO 02/05752 A1 | | 1/2002 |
| WO | WO0205752 | * | 1/2002 |
| WO | WO0215847 | * | 2/2002 |

* cited by examiner

*Primary Examiner* — James Seidleck
*Assistant Examiner* — Peter A Salamon
(74) *Attorney, Agent, or Firm* — Oblon, Spivak, McClelland, Maier & Neustadt, L.L.P.

(57) ABSTRACT

A curable composition for dental use, containing a polymerizable monomer, inorganic particles (A) having irregular shapes and an average particle size of from 1.0 to 5.0 μm, wherein the inorganic particles (A) are surface-treated with a silane coupling agent (a) represented by the formula (I):

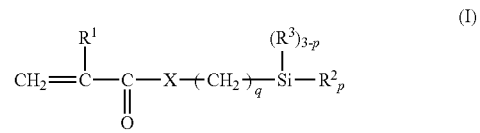

wherein $R^1$ is a hydrogen atom or a methyl group, $R^2$ is a hydrolyzable group, $R^3$ is a hydrocarbon group having 1 to 6 carbon atoms, X is an oxygen or sulfur atom, p is 2 or 3, and q is an integer of from 8 to 13, and inorganic particles (B) having irregular shapes and/or spherical or nearly spherical shapes, and an average particle size of from 0.01 to 0.10 μm, wherein the inorganic particles (B) are surface-treated with a silane coupling agent (b) represented in the same manner as in the silane coupling agent (a) except that q in the formula (I) is an integer of from 1 to 6, wherein the inorganic particles (A) and the inorganic particles (B) are contained in amounts of from 85 to 98% by weight and from 2 to 15% by weight, respectively, of the entire amount of the inorganic particles. The curable composition for dental use of the present invention can be suitably used as a material capable of substituting a part or all of a natural tooth in the field of dental therapy.

7 Claims, No Drawings

CURABLE COMPOSITION FOR DENTAL PURPOSES

TECHNICAL FIELD

The present invention relates to a curable composition for dental use, capable of substituting a part or all of a natural tooth in the field of dental therapy.

BACKGROUND ART

A curable composition for dental use is a composition blended with a polymerizable monomer, a polymerizable initiator, and an inorganic filler, and the composition is the most well used material today as a material for filling and restoring fracture of teeth and dental caries. The composition can exhibit its preferred effect as a material for dental use, by using a specified blending component or adjusting a blending component ratio or the like.

Specifically, Patent Publication 1 discloses a restorative material for dental use satisfying all of high-density packability, high strength, highly aesthetic appreciation, and durability, by combining an inorganic filler treated with a specified silane coupling agent and a strongly hydrophobic polymerizable monomer. In a restorative material for dental use of Patent Publication 2, a mixed filler comprising irregularly shaped inorganic particles, spherical inorganic particles, and fine inorganic particles is used, and surface smoothness can be improved while retaining high fracture toughness and strength by making an average particle size of the irregularly shaped inorganic particles in the mixed filler smaller and using an acyl phosphine oxide as a photopolymerization catalyst.

Patent Publication 1: Japanese Patent Laid-Open No. Hei 2-134307
Patent Publication 2: WO 2002/05752

DISCLOSURE OF INVENTION

Problems to be Solved by the Invention

However, although the composition can be made to have a high strength by adjusting a combination of an inorganic filler and other blending component according to the above efforts, handling property, especially handling property as a direct filling restorative material, has not been satisfactory.

On the other hand, in a conventional curable composition for dental use, especially a composition having a style in which the composition is directly filled into a tooth, a means of lowering an amount of an inorganic filler contained may be considered in order to satisfy handling property; however, only compositions that are less advantageous in values for physical properties such as flexural strength can be obtained. In addition, if an amount of an inorganic filler is increased in order to increase the strength, viscosity of the composition becomes high, so that the composition cannot be used in a directly filling operation to teeth in the treatment.

An object of the present invention is to provide a curable composition for dental use having an appropriate forming property, while having a high strength by containing an inorganic filler at a high level, thereby having excellent handling property.

Means to Solve the Problems

As a result of intensive studies in order to solve the above problems, the present inventors have found that a curable composition for dental use having an appropriate forming property while having a high strength, is obtained, by containing given amounts of inorganic fillers having two different sizes each treated with a specified silane coupling agent, and raising the amounts of the inorganic fillers contained to a high level. The present invention has been perfected thereby.

Specifically, the present invention relates to:
[1] a curable composition for dental use, containing
  a polymerizable monomer,
  inorganic particles (A) having irregular shapes and an average particle size of from 1.0 to 5.0 μm, wherein the inorganic particles (A) are surface-treated with a silane coupling agent (a) represented by the formula (I):

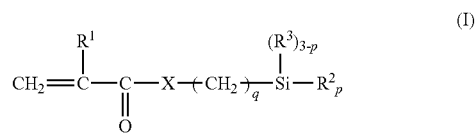

wherein $R^1$ is a hydrogen atom or a methyl group, $R^2$ is a hydrolyzable group, $R^3$ is a hydrocarbon group having 1 to 6 carbon atoms, X is an oxygen or sulfur atom, p is 2 or 3, and q is an integer of from 8 to 13, and
  inorganic particles (B) having irregular shapes and/or spherical or nearly spherical shapes, and an average particle size of from 0.01 to 0.10 μm, wherein the inorganic particles (B) are surface-treated with a silane coupling agent (b) represented in the same manner as in the silane coupling agent (a) except that q in the formula (I) is an integer of from 1 to 6, wherein the inorganic particles (A) and the inorganic particles (B) are contained in amounts of from 85 to 98% by weight and from 2 to 15% by weight, respectively, of the entire amount of the inorganic particles; and
[2] a direct filling restorative material containing the curable composition for dental use as defined above in the item [1].

Effects of the Invention

The curable composition for dental use of the present invention exhibits an excellent effect that the composition has an appropriate forming property while having a high strength by containing inorganic fillers at a high level, so that the composition has excellent handling property.

BEST MODE FOR CARRYING OUT THE INVENTION

In a case where the restoration of teeth is carried out with a conventional curable composition for dental use, since the composition has a high viscosity, the composition cannot be filled directly into the dental cavities from the container housing the composition. Therefore, usually, a method including the steps of taking a composition out in a proper amount from a container to an instrument for dental filling such as an instrument for dental use, filling the composition into the cavities, forming the composition so as to match the cavities, and curing the composition has been carried out. Since the composition for dental use of the present invention has a low viscosity and an appropriate forming property, the composition can be jetted from nozzles having an aperture smaller than the cavity, the nozzles attached to a tip end of the container housing the composition (syringe style container), whereby the composition can be directly filled into the cavity from the syringe. In addition, since the filling procedure can be carried out by simply allowing the composition to pour into the cavity from the syringe, the treatment time can be shortened. In the present specification, as mentioned above, a therapeutic agent capable of directly filling a curable composition for dental use from a container housing the curable composition to a cavity or the like is expressed as a direct filling restorative material.

The curable composition for dental use of the present invention has a great feature in that the curable composition contains a polymerizable monomer and two kinds of inorganic particles having different sizes, each of the inorganic particles being surface-treated with a specified silane coupling agent, and these inorganic particles are each contained in a given amount.

The two kinds of inorganic particles having different sizes in the present invention are inorganic particles (A) having irregular shapes and an average particle size of from 1.0 to 5.0 μm, wherein the inorganic particles (A) are surface-treated with a silane coupling agent (a) represented by the formula (I):

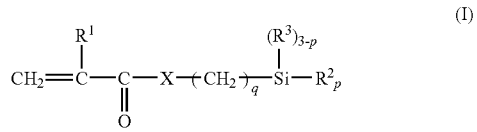

wherein $R^1$ is a hydrogen atom or a methyl group, $R^2$ is a hydrolyzable group, $R^3$ is a hydrocarbon group having 1 to 6 carbon atoms, X is an oxygen or sulfur atom, p is 2 or 3, and q is an integer of from 8 to 13, and inorganic particles (B) having irregular shapes and/or spherical or nearly spherical shapes, and an average particle size of from 0.01 to 0.10 μm, wherein the inorganic particles (B) are surface-treated with a silane coupling agent (b) represented in the same manner as in the silane coupling agent (a) except that q in the formula (I) is an integer of from 1 to 6, and the large inorganic particles treated with a silane coupling agent (a) and the small inorganic particles treated with a silane coupling agent (b) are used together. Here, the inorganic particles having irregular shapes and an average particle size of from 1.0 to 5.0 μm may be referred to herein as a "microfiller," and the inorganic particles having irregular shapes and/or spherical or nearly spherical shapes, and an average particle size of from 0.01 to 0.10 μm may be referred to herein as "fine filler particles."

In general, it has been known that if the surface of inorganic particles is treated with a silane coupling agent, the surface of the inorganic particles is hydrophobically treated, and affinity to a polymerizable monomer is improved, whereby an amount of the inorganic particles contained in the composition can be increased. However, when a microfiller is surface-treated with a silane coupling agent (b) having a short alkyl chain, the amount of the filler contained can be simply increased; however, if the treated microfiller is contained in an amount to an extent that a sufficient strength is exhibited, hydrophobicity of the surface of the microfiller is insufficient, so that a composition having a high viscosity can only be obtained.

In the present invention, in consideration of the above matters, the amount of fillers contained can be increased by treating a microfiller with a silane coupling agent (a) having a long alkyl chain, so that hydrophobicity of the surface of the microfiller is even more increased, whereby a composition having not only a high strength but also a low viscosity could be obtained. However, in the above composition, since the composition has a low viscosity, there is a risk that the composition leaks during use, and in order to prevent leakage, an appropriate forming property is necessary. In view of the above, in the present invention, the fine filler particles are further used as a paste-like adjusting agent of the composition to provide viscosity, thereby securing forming property.

In the present invention, since a high strength is accomplished by containing a microfiller in a large amount, it is necessary to exhibit an effect of the fine filler particles as a thickening agent in a small amount. When the fine filler particles are surface-treated with a silane coupling agent (a), hydrophobicity is increased to have the same level of hydrophobicity as the polymerizable monomer and the microfiller subjected to the specified surface treatment mentioned above, leading to cause the fine filler particles to be undesirably more easily compatible with these components; therefore, the composition cannot be provided with an appropriate forming property with a small amount of addition. On the other hand, when fine filler particles without surface treatment are used, affinity of the fine filler particles to the polymerizable monomer is markedly impaired, so that the fine filler particles are undesirably allowed to separate and precipitate after allowing the composition to stand for a long period of time, thereby making it difficult to obtain a stable composition.

In view of the above, in the present invention, an appropriate hydrophobicity is held by treating the surface of the fine filler particles with a silane coupling agent (b), so that the composition is provided with an appropriate forming property even with addition of a small amount, thereby making it possible to prepare a composition having excellent shape-retaining property.

In the silane coupling agent (a) represented by the general formula (I), $R^1$ is a hydrogen atom or a methyl group, $R^2$ is a hydrolyzable group, $R^3$ is a hydrocarbon group having 1 to 6 carbon atoms, X is an oxygen or sulfur atom, p is 2 or 3, and q is an integer of from 8 to 13. In addition, the hydrolyzable group of $R^2$ includes, for example, alkoxy groups, such as a methoxy group, an ethoxy group, and a butoxy group, a chlorine atom, or an isocyanate group. The hydrocarbon group having 1 to 6 carbon atoms of $R^3$ includes, for example, an alkyl group having 1 to 6 carbon atoms, an alkenyl group having 2 to 6 carbon atoms, an alkynyl group having 2 to 6 carbon atoms, a cycloalkyl group having 3 to 6 carbon atoms, and the like.

The alkyl group having 1 to 6 carbon atoms includes, for example, a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, and an n-hexyl group.

The alkenyl group having 2 to 6 carbon atoms includes, for example, a vinyl group, an allyl group, a methylvinyl group, a propenyl group, a butenyl group, a pentenyl group, a hexenyl group, a cyclopropenyl group, a cyclobutenyl group, a cyclopentenyl group, and a cyclohexenyl group.

The alkynyl group having 2 to 6 carbon atoms includes, for example, an ethynyl, a 1-propynyl, a 2-propynyl, a 1-butynyl, a 1-methyl-2-propynyl, a 2-butynyl, a 3-butynyl, a 1-pentynyl, a 1-ethyl-2-propynyl, a 2-pentynyl, a 3-pentynyl, a 1-methyl-2-butynyl, a 4-pentynyl, a 1-methyl-3-butynyl, a 2-methyl-3-butynyl, a 1-hexynyl, a 2-hexynyl, a 1-ethyl-2-butynyl, a 3-hexynyl, a 1-methyl-2-pentynyl, a 1-methyl-3-pentynyl, a 4-methyl-1-pentynyl, a 3-methyl-1-pentynyl, a 5-hexynyl, and a 1-ethyl-3-butynyl.

The cycloalkyl group having 3 to 6 carbon atoms includes, for example, a cyclopropyl group, a cyclobutyl group, a cyclopentyl group, and a cyclohexyl group.

Specific examples of the silane coupling agent represented by the general formula (I) include 8-methacryloyloxyoctyl trimethoxysilane, 9-methacryloyloxynonyl trimethoxysilane, 10-methacryloyloxydecyl trimethoxysilane, 11-methacryloyloxyundecyl trimethoxysilane, 11-methacryloyloxyundecyl dichloromethylsilane, 11-methacryloyloxyundecyl trichlorosilane, 11-methacryloyloxyundecyl dimethoxymethylsilane, 12-methacryloyloxydodecyl trimethoxysilane, 13-methacryloyloxytridecyl trimethoxysilane, and the like. These silane coupling agents can be used alone or in a proper combination of two or more kinds. Among them, 8-methacryloyloxyoctyl trimethoxysilane, 9-methacryloyloxynonyl trimethoxysilane, 10-methacryloyloxydecyl trimethoxysilane, and 11-methacryloyloxyundecyl trimethoxysilane are preferred, and 11-methacryloyloxyundecyl trimethoxysilane is more preferred, from the viewpoint of satisfying both the containment of the microfiller in a larger amount and low viscosity.

The silane coupling agent (b) is exemplified by the same ones as the silane coupling agent (a), except that q is an integer of from 1 to 6 in the formula (I). Specific examples of the silane coupling agent (b) include methacryloyloxymethyl trimethoxysilane, 2-methacryloyloxyethyl trimethoxysilane, 3-methacryloyloxypropyl trimethoxysilane, 4-methacryloyloxybutyl trimethoxysilane, 5-methacryloyloxypentyl trimethoxysilane, 6-methacryloyloxyhexyl trimethoxysilane, and the like. These silane coupling agents can be used alone or in a proper combination of two or more kinds. Among them, methacryloyloxymethyl trimethoxysilane, 2-methacryloyloxyethyl trimethoxysilane, 3-methacryloyloxypropyl trimethoxysilane, and 4-methacryloyloxybutyl trimethoxysilane are preferred, and 3-methacryloyloxypropyl trimethoxysilane is more preferred, from the viewpoint of providing an appropriate shape-retaining property.

A method for surface-treating inorganic particles with a silane coupling agent is not particularly limited, so long as the method is a method of adsorbing a silane coupling agent to the surface of inorganic particles. The method includes, for example, a method including the steps of spraying a solution prepared by diluting a silane coupling agent with a solvent, while stirring inorganic particles in a mixing vessel, and thermally drying for a certain period of time in the vessel, while continuing to stir; a method including the steps of mixing inorganic particles and a silane coupling agent in a solvent while stirring, and thermally drying the mixture; and the like.

The amount treated with the silane coupling agent (a) in the inorganic particles (A) is preferably from 0.5 to 10 parts by weight, and more preferably from 1 to 5 parts by weight, based on 100 parts by weight of the inorganic particles (A) before the treatment.

The amount treated with the silane coupling agent (b) in the inorganic particles (B) may be properly adjusted by taking into consideration an average particle size of the inorganic particles used or the like, and the amount treated is preferably from 1 to 100 parts by weight, based on 100 parts by weight of the inorganic particles (B) before the treatment.

In the present invention, in order to satisfy both high strength and paste-like state suitable for direct filling by providing the composition with forming property with a small amount of the fine filler particles, while securing strength with a large amount of the microfiller, it is desired that the inorganic particles (A) have larger particle sizes than those of the inorganic particles (B).

In addition, when a spherical filler is used as the inorganic particles (A), it is difficult to increase the strength while maintaining the handling property; therefore, it is necessary that the inorganic particles (A) have irregular shapes. Taking these matters into consideration, the inorganic particles (A) in the present invention have irregular shapes and an average particle size of from 1.0 to 5.0 µm, preferably from 2 to 4 µm, and more preferably from 2 to 3 µm. The average particle size of the inorganic particles (A) is measured in accordance with the method described in Examples set forth below.

On the other hand, the shape of the inorganic particles (B) is not particularly limited, and the inorganic particles (B) having irregular shapes and/or spherical or nearly spherical shapes can be used. The inorganic particles (B) have an average particle size of from 0.01 to 0.10 µm, preferably from 0.01 to 0.06 µm, and more preferably from 0.02 to 0.04 µm. The average particle size of the inorganic particles (B) is measured in accordance with the method described in Examples set forth below.

Here, as to the terms "spherical shapes," "nearly spherical shapes," and "irregular shapes" as used herein, a filler having an average symmetry of 0.9 or more is defined to have "spherical shapes," a filler having an average symmetry of 0.6 or more and less than 0.9 is defined to have "nearly spherical shapes," and a filler having a shape other than the "spherical shapes" and the "nearly spherical shapes" is defined to have "irregular shapes," wherein the average symmetry is calculated by dividing a particle size in the direction perpendicular to a maximum diameter by the maximum diameter, when a maximum diameter is determined by photographing the filler with a scanning electron microscope (hereinafter simply referred to as SEM), and taking the maximum diameter of the rounded particles observed within the unit field of vision.

As to the inorganic particles (A) and (B), since it is presupposed that the inorganic particles are used in the oral cavity, in other words, under wet conditions, it is indispensable that the inorganic particles are insoluble or hardly soluble in water. The inorganic particles include inorganic particles of silica, a mineral containing silica such as kaolin, clay, mica or mica as a base material, ceramics and glass, each containing silica as a base material, and containing $Al_2O_3$, $B_2O_3$, $TiO_2$, $ZrO_2$, $BaO$, $La_2O_3$, $SrO_2$, $CaO$, $P_2O_5$, or the like, including, for example, lanthanum glass ("Schott GM31 684 (registered trademark)" (manufactured by Schott), and the like); barium glass ("Schott GM27 884 (registered trademark)" and "Schott 8253 (registered trademark)" (both manufactured by Schott), and "Ray-Solb E-2000 (registered trademark)" and "Ray-Solb E-3000 (registered trademark)" (both manufactured by Specialty Glass), and the like); strontium glass ("Schott GM32-087 (registered trademark)" (manufactured by Schott) and "Ray-Solb E-4000 (registered trademark)" (manufactured by Specialty Glass) and the like); bio-glass, and the like. In addition, the inorganic particles are exemplified by inorganic particles of hydroxyapatite, alumina, titanium oxide, zirconia, aluminum hydroxide, or the like. These inorganic particles can be used alone or in a combination of two or more kinds. Also, as the inorganic particles used in the present invention, the inorganic particles giving radiopacity can be suitably used. Radiopacity that is significant in dental diagnosis is defined as "radiopacity of the same level as or higher than an aluminum plate having the same thickness as a test material," and the inorganic particles giving the radiopacity as described above generally contain an element heavier than potassium. The inorganic particles giving the radiopacity include, for example, inorganic particles of calcium, titanium, iron, zinc, strontium, zirconium, tin, barium, lanthanum, cerium, ytterbium, hafnium, tungsten, and the like. The inorganic particles may be ground or milled with a vibration ball-mill or the like, to be adjusted to have the average particle size mentioned above.

The composition of the present invention may contain other inorganic particles (C) besides the inorganic particles (A) and the inorganic particles (B), within the range so as not to impair the effects of the present invention. The inorganic particles (C) include inorganic particles of an element heavier than potassium, including, for example, inorganic particles of calcium, titanium, iron, zinc, strontium, zirconium, tin, barium, lanthanum, cerium, ytterbium, hafnium, tungsten, and the like. These inorganic particles can be used alone or in an appropriate combination of two or more kinds.

The inorganic particles (A) are contained in an amount of from 85 to 98% by weight, preferably from 90 to 98% by weight, and more preferably from 92 to 96% by weight, of the entire amount of the inorganic particles.

The inorganic particles (B) are contained in an amount of from 2 to 15% by weight, preferably from 2 to 10% by weight, and more preferably from 4 to 8% by weight, of the entire amount of the inorganic particles.

The inorganic particles in the composition of the present invention are contained in a total amount of preferably from 75 to 90% by weight, and more preferably from 78 to 82% by weight.

The polymerizable monomer in the present invention is not particularly limited, and a known one can be used. The polymerizable monomer includes, for example, a polymerizable monomer (A) having an aromatic ring without having any hydroxyl groups, a polymerizable monomer (B) having an aromatic ring and a hydroxyl group, a polymerizable monomer (C) without having any aromatic rings and any hydroxyl groups, and the like.

The polymerizable monomer (A) having an aromatic ring without having any hydroxyl groups is not particularly limited, so long as the polymerizable monomer has an aromatic ring without having any hydroxyl groups, and the polymerizable monomer may have at least one aromatic ring. The compound includes a compound represented by the formula (II):

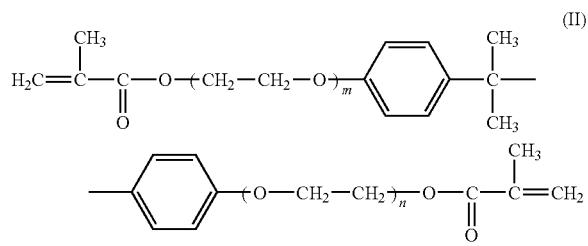

wherein m and n are positive numbers showing an average number of moles of an ethoxy group added, wherein the sum of m and n is preferably from 1 to 6, and more preferably from 2 to 4, including, for example, 2,2-bis[4-(meth)acryloyloxypolyethoxyphenyl]-propane in which m and n satisfy the formula of m+n=2.6 (which may be hereinafter referred to as D2.6E); 2,2-bis[4-(meth)acryloyloxypolyethoxyphenyl]propane in which m and n satisfy the formula of m+n=6 (which may be hereinafter referred to as D6E); 2,2-bis[4-(meth)acryloyloxyphenyl]propane (m and n satisfy the formula of m+n=0); 2,2-bis[4-(meth)acryloyloxydiethoxyphenyl]propane (m and n satisfy the formula of m+n=2), 2,2-bis[4-(meth)acryloyloxytetraethoxyphenyl]propane (m and n satisfy the formula of m+n=4), 2,2-bis[4-(meth)acryloyloxypentaethoxyphenyl]propane (m and n satisfy the formula of m+n=5). In addition, the compound includes, for example, 2,2-bis[(meth)acryloyloxyphenyl]propane, 2,2-bis[4-(meth)acryloyloxydipropoxyphenyl]propane, 2-[4-(meth)acryloyloxydiethoxyphenyl]-2-[4-(meth)acryloyloxyditriethoxyphenyl]propane, 2-[4-(meth)acryloyloxydipropoxyphenyl]-2-[4-(meth)acryloyloxytriethoxyphenyl]propane, 2,2-bis[4-(meth)acryloyloxypropoxyphenyl]propane, 2,2-bis[4-(meth)acryloyloxyisopropoxyphenyl]propane, and 2,2-bis[4-[3-(meth)acryloyloxy-2-(meth)acryloyloxypropoxy]phenyl]propane.

The polymerizable monomer (B) having an aromatic ring and a hydroxyl group is not particularly limited, so long as the polymerizable monomer has an aromatic ring and a hydroxyl group, and the number of aromatic rings and the number of hydroxyl groups are respectively independent numbers, and the polymerizable monomer may have at least one of both the functional groups. The compound includes, for example, 2,2-bis[4-[3-(meth)acryloyloxy-2-hydroxypropoxy]phenyl]propane (which may be hereinafter referred to as Bis-GMA) and 1,2-bis[3-(meth)acryloyloxy-2-hydroxypropoxy]ethane.

The polymerizable monomer (C) without having any aromatic rings and any hydroxyl groups includes, for example, ethylene glycol di(meth)acrylate, triethylene glycol di(meth)acrylate (which may be hereinafter referred to as 3G), propylene glycol di(meth)acrylate, neopentyl glycol di(meth)acrylate, 1,6-hexanediol di(meth)acrylate, 1,10-decanediol di(meth)acrylate (which may be hereinafter referred to as DD), methyl (meth)acrylate, iso-butyl (meth)acrylate, benzyl (meth)acrylate, lauryl (meth)acrylate, 2-(N,N-dimethylamino)ethyl (meth)acrylate, 2,3-dibromopropyl (meth)acrylate, N,N'-(2,2,4-trimethylhexamethylene) bis[2-(aminocarboxy)ethan-1-ol]dimethacrylate, N,N'-(2,2,4-trimethylhexamethylene) bis[2-(aminocarboxy)propane-1,3-diol]tetramethacrylate (which may be hereinafter referred to as U4TH), (meth)acryloyloxydodecylpyridinium bromide, (meth)acryloyloxydodecylpyridinium chloride, trimethylolpropane tri(meth)acrylate, trimethylolethane tri(meth)acrylate, and pentaerythritol tetra(meth)acrylate. Here, the term "(meth)acrylate" refers to an acrylic acid ester and/or a methacrylic acid ester.

A polymerizable monomer other than the polymerizable monomers (A), (B), and (C) which can be used in the present invention includes, for example, esters (meth)acrylamide of α-cyanoacrylic acid, (meth)acrylic acid, α-halogenated acrylic acids, crotonic acid, cinnamic acid, sorbic acid, maleic acid, itaconic acid, and the like, (meth)acrylamide derivatives, vinyl esters, vinyl ethers, mono-N-vinyl derivatives, and styrenic derivatives, among which the (meth)acrylic acid ester is preferably used.

The polymerizable monomer is used singly or in a combination of several kinds, and as the polymerizable monomer, a known monomer in the dental material is used without particular limitation.

The polymerizable monomer is contained in a total amount of preferably from 12 to 30 parts by weight, and more preferably from 17 to 27 parts by weight, based on 100 parts by weight of the entire amount of the inorganic particles, from the viewpoint of obtaining suitable handling property in a case of carrying out direct filling.

In addition, in the present invention, the polymerizable monomer has a viscosity at 40° C. of preferably from 20 to 400 mPa·s, and more preferably from 40 to 200 mPa·s, from the viewpoint of obtaining suitable handling property in a case of carrying out direct filling. Here, in a case where two or more kinds of polymerizable monomers are used, the viscosity of the overall polymerizable monomer can be expressed by a weighted average viscosity of the polymerizable monomers, and the polymerizable monomers have an average viscosity at 40° C. of preferably from 20 to 400 mPa·s, and more preferably from 40 to 200 mPa·s. In the present specification, the viscosity of the polymerizable monomer is measured in accordance with the method described in Examples set forth below.

The polymerization of the polymerizable monomer can be carried out in accordance with a known method using a polymerization initiator, if necessary.

As the polymerization initiator, a known polymerization initiator can be used, and the polymerization initiator is usually selected taking into consideration the polymerizability of the polymerizable monomer and the polymerization conditions.

In a case where the polymerization is carried out at an ambient temperature, for example, a redox polymerization initiator, such as an organic peroxide/amine mixture or an organic peroxide/amine/sulfinic acid (or a salt thereof) mixture is preferably used. When the redox polymerization initiator is used, it is necessary to have a wrapping form in which an oxidizing agent and a reducing agent are separately wrapped, to mix both the components immediately before use. The oxidizing agent includes organic peroxides such as diacyl peroxides, peroxy esters, dialkyl peroxides, peroxy ketals, ketone peroxides, and hydroperoxides. Specifically, the diacyl peroxide includes benzoyl peroxide, 2,4-dichlorobenzoyl peroxide, m-toluoyl peroxide, and the like. The peroxy ester includes, for example, t-butylperoxy benzoate, bis-t-butylperoxy isophthalate, 2,5-dimethyl-2,5-bis(benzoylperoxy)hexane, t-butylperoxy-2-ethyl hexanoate, and t-butylperoxy isopropyl carbonate. The dialkyl peroxide includes, for example, dicumyl peroxide, di-t-butyl peroxide, and lauroyl peroxide. The peroxy ketal includes, for example, 1,1-bis(t-butylperoxy) 3,3,5-trimethylcyclohexane. The ketone peroxide includes, for example, methyl ethyl ketone peroxide. The hydroperoxide includes, for example, t-butyl hydroperoxide. As the reducing agent, a tertiary amine is usually used, and the tertiary amine includes, for example, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-i-propylaniline, N,N-dimethyl-4-t-butylaniline, N,N-dimethyl-3,5-di-t-butylaniline, N,N-di(2-hydroxyethyl)-p-toluidine, N,N-di(2-hydroxyethyl)-3,5-dimethylaniline, N,N-di(2-hydroxyethyl)-3,4-dimethylaniline, N,N-di(2-hydroxyethyl)-4-ethylaniline, N,N-di(2-hydroxyethyl)-4-i-propylaniline, N,N-di(2-hydroxyethyl)-4-t-butylaniline, N,N-di(2-hydroxyethyl)-3,5-di-1-propylaniline, N,N-di(2-hydroxyethyl)-3,5-di-t-butylaniline, ethyl 4-dimethylaminobenzoate, n-butoxyethyl 4-dimethylaminobenzoate, (2-methacryloyloxy)ethyl 4-dimethylaminobenzoate, trimethylamine, triethylamine, N-methyldiethanolamine, N-ethyldiethanolamine, N-n-butyldiethanolamine, N-lauryldiethanolamine, triethanolamine, (2-dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, and the like. Besides the above, an oxidation-reduction initiator, such as a cumene hydroperoxide/thiourea mixture, an ascorbic acid/$Cu^{2+}$ salt mixture, and an organosulfinic acid (or a salt thereof)/amine/peroxide, tributylborane, an organosulfinic acid or the like is suitably used.

When a photopolymerization by irradiation with visible light is carried out, an oxidation-reduction initiator, such as an α-diketone/tertiary amine, an α-diketone/aldehyde, or an α-diketone/mercaptan is preferred. The photopolymerization initiator includes, for example, an α-diketone/reducing agent, a ketal/reducing agent, a thioxanthone/reducing agent, and the like. Examples of the α-diketone include camphorquinone, benzyl, 2,3-pentanedione, and the like. Examples of the ketal include benzyl dimethyl ketal, benzyl diethyl ketal, and the like. Examples of the thioxanthone include 2-chlorothioxanthone, 2,4-diethylthioxanthone, and the like. Examples of the reducing agent include a Michler's ketone, and the like; tertiary amines such as 2-(dimethylamino)ethyl methacrylate, N,N-bis[(meth)acryloyloxyethyl]-N-methylamine, ethyl N,N-dimethylaminobenzoate, butyl 4-dimethylaminobenzoate, butoxyethyl 4-dimethylaminobenzoate, N-methyldiethanolamine, 4-dimethylaminobenzophenone, N,N-di(2-hydroxyethyl)-p-toluidine, and dimethylaminophenanthrol; aldehydes such as citronellal, lauryl aldehyde, phthaldialdehyde, dimethylaminobenzaldehyde, and terephthalaldehyde; compounds having a thiol group, such as thiosalicylic acid, thiobenzoic acid, and the like, for example, 2-mercaptobenzooxazole, decanethiol, 3-mercaptopropyl trimethoxysilane, 4-mercaptoacetophenone, or the like; and the like. An α-diketone/organic peroxide/reducing agent mixture obtained by adding an organic peroxide to these oxidation-reduction systems is also preferably used.

When a photopolymerization by irradiation with ultraviolet light is carried out, an alkyl ether of benzoin, benzyl dimethyl ketal, or the like is preferred. Further, an acyl phosphine oxide photopolymerization initiator is preferably used. The acyl phosphine oxide includes, for example, benzoyl methyl ether, 2,4,6-trimethylbenzoyl diphenyl phosphine oxide, 2,6-dimethoxybenzoyl diphenyl phosphine oxide, 2,6-dichlorobenzoyl diphenyl phosphine oxide, 2,3,5,6-tetramethylbenzoyl diphenyl phosphine oxide, benzoyl di-(2,6-dimethylphenyl) phosphonate, and 2,4,6-trimethylbenzoyl ethoxyphenyl phosphine oxide. These acyl phosphine oxide polymerization initiators can be used alone, or together with a reducing agent, such as various amines, aldehydes, mercaptans, and sulfinates. The acyl phosphine oxide polymerization initiator can be suitably used together with the photopolymerization initiator of the visible light.

The polymerization initiators can be used alone or in an appropriate combination of two or more kinds. The polymerization initiators are contained in a total amount of preferably from 0.1 to 10 parts by weight, and more preferably from 0.2 to 5.0 parts by weight, based on 100 parts by weight of the entire amount of the polymerizable monomers.

The composition of the present invention may be blended, besides the polymerizable monomer and the inorganic particles, with an additive, such as a polymerization inhibitor, an ultraviolet absorbent, a fluorescent agent, or a pigment as a raw material.

The polymerization inhibitor includes, for example, 2,6-dibutylhydroxytoluene, hydroquinone, dibutylhydroquinone, dibutylhydroquinone monomethyl ether, 2,6-t-butylphenol, and the like. These polymerization inhibitors may be blended alone or in a combination of two or more kinds.

The composition of the present invention is not particularly limited, so long as the composition contains the polymerizable monomer and given amounts of the inorganic particles (A) and (B), and can be easily produced by a method known to one of ordinary skill in the art in a state according to the application (one paste-like state, two paste-like state, powder-liquid state, molded state). Here, when a chemical polymerizability function or a combined polymerization initiation function having both a chemical polymerizability and photopolymerizability is used, it is necessary that a composition containing an organic peroxide and a composition containing a reducing agent have a wrapping form in which the compositions are separately wrapped, and both the compositions are mixed immediately before use.

The composition of the present invention, especially when used as a direct filling restorative material, has a viscosity of preferably from 20 to 700 Pa·s, and more preferably from 60 to 400 Pa·s, from the viewpoint of handling property. Here, the viscosity of the composition as used herein is measured in accordance with the method described in Examples set forth below.

In one embodiment of the composition of the present invention, a time period during which tan δ of storage modulus (G') and loss modulus (G") obtained under the measurement conditions described later, i.e. tan δ [(G")/(G')], satisfies 1 or less is preferably from 5 to 60 seconds, more preferably from 10 to 40 seconds, and even more preferably from 10 to 20 seconds, from the viewpoint of being capable of filling the composition without leaking the paste upon the filling operation. Here, the storage modulus (G') shows a degree to which the composition acts like an elastic member, and the loss modulus (G") shows a degree to which the composition acts like a viscous member, and a time period during which tan δ [(G")/(G')] satisfies 1 or less means a time period from a state of a composition having an even lower viscosity in a manner that the property of the viscous member is stronger than that of the elastic member to a state where a composition begins to show an appropriately low viscosity in a manner that the property of the elastic member begins to be stronger than that of the viscous member. Specifically, the time period taken is equivalent to a time period from a point after pushing out the composition from a syringe to a time when a composition shows a property of the elastic member is stronger, or to a time point when a composition begins to show forming property without leaking, in a case of a fast recovery of a property of the elastic member. In this measurement of dynamic viscoelasticity, the composition is likely to be strained upon pushing out the composition from the syringe, and the structure is broken, so that as shown in the measurement conditions described later, the measurement is begun after application of a given strain, which is a parameter that serves as an index of change in viscoelasticity after pushing out the composition from the syringe.

Further, in one embodiment of the composition of the present invention, tan δ of storage modulus (G') and loss modulus (G"), i.e. tan δ [(G")/(G')], is preferably from 0.5 to 1.0, more preferably from 0.7 to 1.0, even more preferably from 0.8 to 1.0, and still even more preferably from 0.9 to 1.0, after 70 seconds from the beginning of the measurement, from the viewpoint of having flowability that is capable of filling to the corners of the cavity. Specifically, when the recovery to the elastic member is too soon during the period of the beginning to the end of filling, the flowability of the paste is drastically worsened, so that the paste may not be filled to the corners of the cavity, especially an acute angle part. When the paste recovers the structure in one hand, and the paste maintains flowability which is a property of the viscous member, the paste can then be filled to the corners of the cavity. If the composition has the value within the range after 70 seconds from the beginning of the measurement, the composition shows a flow condition that is capable of sufficiently filling to the corners of the cavity, while maintaining a state that the composition provides forming property without leaking, so that the composition is provided with handling property more excellent than conventional compositions.

EXAMPLES

Average Particle Size of Inorganic Particles (A)

Measurement Method 1

The average particle size of the inorganic particles (A) refers to a volume-median particle size, and the volume-median particle size means a particle size of which cumulative volume frequency calculated on a volume percentage is 50% counted from the smaller particle sizes.

Measurement Apparatus: Model CAPA500 (manufactured by Horiba, LTD.)

Analyzing Software: Light Transmission Centrifugal Precipitation Method

Dispersion: 0.2% Sodium hexametaphosphate

Dispersion Conditions: A 15 mg sample is added to 20 mL of the above dispersion, and the mixture is dispersed with an ultrasonic disperser, to prepare a sample-containing dispersion.

Measurement Conditions The above sample-containing dispersion is measured to obtain a volume-median particle size and a ratio of the number of particles having a particle size of from 0.01 to 100 µm.

Average Particle Size of Inorganic Particles (B)

Measurement Method 2

Using a high-performance scanning electron microscope (S-4500, manufactured by HITACHI, LTD.), a filler is observed under the condition of an acceleration voltage of 15 kV, and an image having a magnification of 10,000 folds is obtained. Using an image-analyzing particle size distribution measurement software (MAC-View Ver. 3.5, manufactured by MOUNTECH Co., Ltd.), randomly selected 100 particles are measured, and a volume-median particle size is obtained from the volume distribution.

[Viscosity of Polymerizable Monomer]

A prepared monomer is placed on a viscosity measurement apparatus (Model TV-30 viscometer, manufactured by TOKI SANGYO CO., LTD.), and the measurement of viscosity is taken while retaining the temperature at 40° C. The measurement is carried out under conditions of a cone diameter of 48 mm, an angle of inclination of the cone of 0.8°, and a rotational speed of 100 r/min.

[Viscosity of Composition]

A prepared paste is placed on a rheometer (AR2000, manufactured by TA Instruments, Japan), and the measurement of viscosity is taken while holding the temperature at 25° C. The measurement is carried out under conditions of a diameter of a parallel plate of 20 mm and a shearing rate of 1.0 sec$^{-1}$ by rotating the plates in a given direction.

Production Example 1 of Inorganic Particles

Barium glass "Ray-Solb E-3000" (manufactured by Specialty Glass) was ground or milled with a vibration ball-mill, to give a fine inorganic particle powder having an irregular shape, the fine inorganic particle powder having a volume-median particle size of 2.5 µm and containing the number of particles having particle sizes of from 0.2 to 50 µm in a proportion of 99% by volume. A three-neck flask was charged with 100 g of the resulting inorganic particles having irregular shapes, the inorganic particles having an average particle size of 2.5 µm, 2.0 g of 11-methacryloyloxyundecyl trimethoxysilane, and 200 mL of toluene, and the components were stirred at room temperature for 2 hours. The toluene was distilled off under a reduced pressure, and the residue was then subjected to vacuum drying at 40° C. for 16 hours. Further, the dried residue was heated at 90° C. for 3 hours, to give inorganic particles (a-1) having an average particle size of 2.5 μm.

Production Example 2 of Inorganic Particles

Barium glass "Ray-Solb E-3000" (manufactured by Specialty Glass) was ground or milled with a vibration ball-mill, to give a fine inorganic particle powder having an irregular shape, the fine inorganic particle powder having a volume-median particle size of 2.5 μm and containing the number of particles having particle sizes of from 0.2 to 50 μm in a proportion of 99% by volume. A three-neck flask was charged with 100 g of the resulting inorganic particles having irregular shapes, the inorganic particles having an average particle size of 2.5 μm, 2.0 g of 3-methacryloyloxypropyl trimethoxysilane, and 200 mL of toluene, and the components were stirred at room temperature for 2 hours. The toluene was distilled off under a reduced pressure, and the residue was then subjected to vacuum drying at 40° C. for 16 hours. Further, the dried residue was heated at 90° C. for 3 hours, to give inorganic particles (a-2) having an average particle size of 2.5 μm.

Production Example 3 of Inorganic Particles

Barium glass "Ray-Solb E-3000" (manufactured by Specialty Glass) was ground or milled with a vibration ball-mill, to give a fine inorganic particle powder having an irregular shape, the fine inorganic particle powder having a volume-median particle size of 2.5 μm and containing the number of particles having particle sizes of from 0.2 to 50 μm in a proportion of 99% by volume. A three-neck flask was charged with 100 g of the resulting inorganic particles having irregular shapes, the inorganic particles having an average particle size of 2.5 μm, 2.0 g of 8-methacryloyloxyoctyl trimethoxysilane, and 200 mL of toluene, and the components were stirred at room temperature for 2 hours. The toluene was distilled off under a reduced pressure, and the residue was then subjected to vacuum drying at 40° C. for 16 hours. Further, the dried residue was heated at 90° C. for 3 hours, to give inorganic particles (a-3) having an average particle size of 2.5 μm.

Production Example 4 of Inorganic Particles

Barium glass "Ray-Solb E-3000" (manufactured by Specialty Glass) was ground or milled with a vibration ball-mill, to give a fine inorganic particle powder having an irregular shape, the fine inorganic particle powder having a volume-median particle size of 2.5 μm and containing the number of particles having particle sizes of from 0.2 to 50 μm in a proportion of 99% by volume. A three-neck flask was charged with 100 g of the resulting inorganic particles having irregular shapes, the inorganic particles having an average particle size of 2.5 μm, 2.0 g of 13-methacryloyloxytridecyl trimethoxysilane, and 200 mL of toluene, and the components were stirred at room temperature for 2 hours. The toluene was distilled off under a reduced pressure, and the residue was then subjected to vacuum drying at 40° C. for 16 hours. Further, the dried residue was heated at 90° C. for 3 hours, to give inorganic particles (a-4) having an average particle size of 2.5 μm.

Production Example 5 of Inorganic Particles

Barium glass "Ray-Solb E-3000" (manufactured by Specialty Glass) was ground or milled with a vibration ball-mill, to give a fine inorganic particle powder having an irregular shape, the fine inorganic particle powder having a volume-median particle size of 2.5 μm and containing the number of particles having particle sizes of from 0.2 to 50 μm in a proportion of 99% by volume. A three-neck flask was charged with 100 g of the resulting inorganic particles having irregular shapes, the inorganic particles having an average particle size of 2.5 μm, 0.8 g of 11-methacryloyloxyundecyl trimethoxysilane, and 200 mL of toluene, and the components were stirred at room temperature for 2 hours. The toluene was distilled off under a reduced pressure, and the residue was then subjected to vacuum drying at 40° C. for 16 hours. Further, the dried residue was heated at 90° C. for 3 hours, to give inorganic particles (a-5) having an average particle size of 2.5 μm.

Production Example 6 of Inorganic Particles

Barium glass "Ray-Solb E-3000" (manufactured by Specialty Glass) was ground or milled with a vibration ball-mill, to give a fine inorganic particle powder having an irregular shape, the fine inorganic particle powder having a volume-median particle size of 2.5 μm and containing the number of particles having particle sizes of from 0.2 to 50 μm in a proportion of 99% by volume. A three-neck flask was charged with 100 g of the resulting inorganic particles having irregular shapes, the inorganic particles having an average particle size of 2.5 μm, 6 g of 11-methacryloyloxyundecyl trimethoxysilane, and 200 mL of toluene, and the components were stirred at room temperature for 2 hours. The toluene was distilled off under a reduced pressure, and the residue was then subjected to vacuum drying at 40° C. for 16 hours. Further, the dried residue was heated at 90° C. for 3 hours, to give inorganic particles (a-6) having an average particle size of 2.5 μm.

Production Example 7 of Inorganic Particles

Barium glass "Ray-Solb E-3000" (manufactured by Specialty Glass) was ground or milled with a vibration ball-mill, to give a fine inorganic particle powder having an irregular shape, the fine inorganic particle powder having a volume-median particle size of 1.0 μm and containing the number of particles having particle sizes of from 0.2 to 50 μm in a proportion of 99% by volume. A three-neck flask was charged with 100 g of the resulting inorganic particles having irregular shapes, the inorganic particles having an average particle size of 1.0 μm, 2.0 g of 11-methacryloyloxyundecyl trimethoxysilane, and 200 mL of toluene, and the components were stirred at room temperature for 2 hours. The toluene was distilled off under a reduced pressure, and the residue was then subjected to vacuum drying at 40° C. for 16 hours. Further, the dried residue was heated at 90° C. for 3 hours, to give inorganic particles (a-7) having an average particle size of 1.0 μm.

Production Example 8 of Inorganic Particles

Barium glass "Ray-Solb E-3000" (manufactured by Specialty Glass) was ground or milled with a vibration ball-mill, to give a fine inorganic particle powder having an irregular shape, the fine inorganic particle powder having a volume-median particle size of 5.0 μm and containing the number of particles having particle sizes of from 0.2 to 50 μm in a proportion of 99% by volume. A three-neck flask was charged with 100 g of the resulting inorganic particles having irregular shapes, the inorganic particles having an average particle size of 5.0 μm, 2.0 g of 11-methacryloyloxyundecyl trimethoxysilane, and 200 mL of toluene, and the components were stirred at room temperature for 2 hours. The toluene was distilled off under a reduced pressure, and the residue was then subjected to vacuum drying at 40° C. for 16 hours. Further, the dried residue was heated at 90° C. for 3 hours, to give inorganic particles (a-8) having an average particle size of 5.0 μm.

Production Example 9 of Inorganic Particles

A three-neck flask was charged with 100 g of an inorganic filler ("KE-P250" silica, manufactured by Nippon Shokubai) having a spherical shape, the inorganic filler having an average particle size of 2.5 μm, 2 g of 11-methacryloyloxyundecyl trimethoxysilane, and 200 mL of toluene, and the components were stirred at room temperature for 2 hours. The toluene was distilled off under a reduced pressure, and the residue was then subjected to vacuum drying at 40° C. for 16 hours. Further, the dried residue was heated at 90° C. for 3 hours, to give inorganic particles (a-9) having an average particle size of 2.5 μm.

Production Example 10 of Inorganic Particles

A flask was charged with 100 g of a fine particle filler ("Ar130" silica, manufactured by Nihon Aerosil Co., Ltd.) having a nearly spherical shape, the fine particle filler having an average particle size of 0.02 μm, 40 g of 11-methacryloyloxyundecyl trimethoxysilane, and 610 mL of toluene, and the components were vigorously stirred at 30° C. for 20 minutes. The toluene was distilled off under a reduced pressure at 30° C., and the residue was then subjected to vacuum drying, to give inorganic particles (b-1) having an average particle size of 0.02 μm.

Production Example 11 of Inorganic Particles

A flask was charged with 100 g of a fine particle filler ("Ar130" silica, manufactured by Nihon Aerosil Co., Ltd.) having a nearly spherical shape, the fine particle filler having an average particle size of 0.02 μm, 40 g of 3-methacryloyloxypropyl trimethoxysilane, and 610 mL of toluene, and the components were vigorously stirred at 30° C. for 20 minutes. The toluene was distilled off under a reduced pressure at 30° C., and the residue was then subjected to vacuum drying, to give inorganic particles (b-2) having an average particle size of 0.02 μm.

Production Example 12 of Inorganic Particles

A flask was charged with 100 g of a fine particle filler ("Ar130" silica, manufactured by Nihon Aerosil Co., Ltd.) having a nearly spherical shape, the fine particle filler having an average particle size of 0.02 μm, 40 g of 1-methacryloyloxymethyl trimethoxysilane, and 610 mL of toluene, and the components were vigorously stirred at 30° C. for 20 minutes. The toluene was distilled off under a reduced pressure at 30° C., and the residue was then subjected to vacuum drying, to give inorganic particles (b-3) having an average particle size of 0.02 μm.

Production Example 13 of Inorganic Particles

A flask was charged with 100 g of a fine particle filler ("Ar130" silica, manufactured by Nihon Aerosil Co., Ltd.) having a nearly spherical shape, the fine particle filler having an average particle size of 0.02 μm, 40 g of 5-methacryloxypentyl trimethoxysilane, and 610 mL of toluene, and the components were vigorously stirred at 30° C. for 20 minutes. The toluene was distilled off under a reduced pressure at 30° C., and the residue was then subjected to vacuum drying, to give inorganic particles (b-4) having an average particle size of 0.02 μm.

Production Example 1 of Polymerizable Monomer Composition

Polymerizable monomers listed in Table 1 or 2, and 0.15 parts by weight of camphorquinone, 0.175 parts by weight of ethyl N,N-dimethylaminobenzoate, and 0.0125 parts by weight of butyl hydroxytoluene (BHT), based on 25 parts by weight of a total amount of the polymerizable monomers were mixed together, to give a polymerizable monomer composition.

Examples 1 to 18 and Comparative Examples 1 to 9

The inorganic particles listed in Table 1 or 2 and a polymerizable monomer composition were mixed together, to prepare a paste-like composite resin for dental use of each of Examples 1 to 18 and Comparative Examples 1 to 9.

Test Example 1

Forming Property

The shape of the paste upon pushing out the paste obtained on a flat plate from a needle with a needle tip having a tip end diameter of 0.80 mm was visually observed, and the forming property was evaluated in accordance with the following evaluation criteria. The results are shown in Tables 1 and 2. Here, those evaluated with 2 to 5 are considered as acceptable products.

[Evaluation Criteria for Forming Property]
1: A hemispherical shape is not formed, and the shape that is pushed out is maintained.
2: While a hemispherical shape is formed, a shape that is pushed out slightly remains.
3: A hemisphere is formed, and its shape in that state is maintained.
4: A hemisphere is formed, and a height is slightly lowered.
5: A hemisphere is formed, and a height is lowered.
6: A hemisphere is not formed, or a hemisphere is immediately crushed even if it is formed.

Test Example 2

Consistency

The paste obtained was allowed to stand in a thermostat at 60° C. (humidity: 40%) for 5 days, the paste was then allowed to stand at 25° C. for 2 hours, and a consistency test was carried out for the paste. A 0.5 mL paste was measured out, and gently placed on a glass plate (5 cm×5 cm) in a manner that the paste was cast up in the center of the glass plate in a thermostatic chamber at 25° C. (humidity: 40%). A 40 g glass plate (5 cm×5 cm) was placed thereon, and the length and the breadth of the paste after passage of 120 seconds were measured over the glass plate, and an arithmetic means of the both was calculated, and defined as a consistency. The results are shown in Tables 1 and 2. Those cases where a consistency is from 22 to 40 mm are considered as acceptable products.

Test Example 3

Flexural Strength

The paste obtained was filled in a stainless steel die (dimensions: 2 mm×2 mm×25 mm), and top and bottom of the die were pressed with slide glass. The pressed paste was irradiated with light for 2 minutes each from both the sides with a photoirradiation instrument for dental technique (ALPHA-LIGHT II, manufactured by MORITA) to cure. For each of Examples and Comparative Examples, five sets of cured products were prepared, and each cured product was taken out of the die, and then stored in distilled water at 37° C. The flexural strength was measured using an Instron tensile tester under the conditions of a span of 20 mm and a crosshead speed of 1 mm/min, and an average of the found values for each test piece was calculated and defined as flexural strength. The results are shown in Tables 1 and 2. Here, cases where flexural strength is 130 MPa or more are considered as acceptable products.

TABLE 1

| Components of Curable Composition for Dental Use | | Examples | | | | | | | | | |
|---|---|---|---|---|---|---|---|---|---|---|---|
| | | 1 | 2 | 3 | 4 | 5 | 6 | 7 | 8 | 9 | 10 |
| Inorganic Particles | a-1 | 94 | 97 | 85 | 94 | 94 | 94 | 94 | 94 | — | — |
| | a-2 | — | — | — | — | — | — | — | — | — | — |
| | a-3 | — | — | — | — | — | — | — | — | 94 | — |
| | a-4 | — | — | — | — | — | — | — | — | — | 94 |
| | a-5 | — | — | — | — | — | — | — | — | — | — |
| | a-6 | — | — | — | — | — | — | — | — | — | — |
| | a-7 | — | — | — | — | — | — | — | — | — | — |
| | a-8 | — | — | — | — | — | — | — | — | — | — |
| | a-9 | — | — | — | — | — | — | — | — | — | — |
| | b-1 | — | — | — | — | — | — | — | — | — | — |
| | b-2 | 6 | 3 | 15 | 6 | 6 | 6 | 6 | 6 | 6 | 6 |
| | b-3 | — | — | — | — | — | — | — | — | — | — |
| | b-4 | — | — | — | — | — | — | — | — | — | — |
| Polymerizable Monomer Composition | D2.6E | 18.75 | 18.75 | 18.75 | 15 | 22 | 25 | 18.75 | — | 18.75 | 18.75 |
| | Bis-GMA | — | — | — | — | — | — | — | — | — | — |
| | 3G | 6.25 | 6.25 | 6.25 | 10 | 3 | — | — | 6.25 | 6.25 | 6.25 |
| | DD | — | — | — | — | — | — | 6.25 | — | — | — |
| | U4TH | — | — | — | — | — | — | — | 18.75 | — | — |
| | Viscosity (mPa·s)[1] | 54 | 54 | 54 | 28 | 103 | 228 | 119 | 212 | 54 | 54 |
| Physical Properties | | | | | | | | | | | |
| Forming Property | | 3 | 5 | 2 | 5 | 3 | 2 | 3 | 2 | 2 | 4 |
| Consistency (mm) | | 33 | 40 | 22 | 37 | 28 | 25 | 34 | 24 | 25 | 38 |
| Flexural Strength (MPa) | | 150 | 141 | 132 | 135 | 153 | 160 | 143 | 140 | 155 | 135 |
| Viscosity of Composition (Pa·s) | | 123 | 25 | 653 | 20 | 147 | 395 | 113 | 475 | 413 | 45 |

| Components of Curable Composition for Dental Use | | Examples | | | | | | | |
|---|---|---|---|---|---|---|---|---|---|
| | | 11 | 12 | 13 | 14 | 15 | 16 | 17 | 18 |
| Inorganic Particles | a-1 | — | — | 94 | 94 | — | — | 94 | 94 |
| | a-2 | — | — | — | — | — | — | — | — |
| | a-3 | — | — | — | — | — | — | — | — |
| | a-4 | — | — | — | — | — | — | — | — |
| | a-5 | 94 | — | — | — | — | — | — | — |
| | a-6 | — | 94 | — | — | — | — | — | — |
| | a-7 | — | — | — | — | 94 | — | — | — |
| | a-8 | — | — | — | — | — | 94 | — | — |
| | a-9 | — | — | — | — | — | — | — | — |
| | b-1 | — | — | — | — | — | — | — | — |
| | b-2 | 6 | 6 | — | — | 6 | 6 | 6 | 6 |
| | b-3 | — | — | 6 | — | — | — | — | — |
| | b-4 | — | — | — | 6 | — | — | — | — |
| Polymerizable Monomer Composition | D2.6E | 18.75 | 18.75 | 18.75 | 18.75 | 18.75 | 18.75 | — | 9.37 |
| | Bis-GMA | — | — | — | — | — | — | 18.75 | 9.38 |
| | 3G | 6.25 | 6.25 | 6.25 | 6.25 | 6.25 | 6.25 | 6.25 | 6.25 |
| | DD | — | — | — | — | — | — | — | — |
| | U4TH | — | — | — | — | — | — | — | — |
| | Viscosity (mPa·s)[1] | 54 | 54 | 54 | 54 | 54 | 54 | 300 | 164 |
| Physical Properties | | | | | | | | | |
| Forming Property | | 2 | 3 | 2 | 5 | 2 | 4 | 4 | 4 |
| Consistency (mm) | | 26 | 36 | 27 | 40 | 25 | 38 | 40 | 38 |
| Flexural Strength (MPa) | | 148 | 148 | 138 | 155 | 133 | 158 | 157 | 146 |
| Viscosity of Composition (Pa·s) | | 300 | 80 | 160 | 23 | 450 | 32 | 188 | 43 |

\* The amount of the raw materials of the composition used is expressed by parts by weight.
\* Polymerizable monomer: D2.6E: 2,2-Bis[4-(meth)acryloyloxypolyethoxyphenyl]propane, Bis-GMA: 2,2-bis[4-[3-(meth)acryloyloxy-2-hydroxypropoxy]phenyl]propane, 3G: Triethylene glycol di(meth)acrylate, DD: 1,10-decanediol di(meth)acrylate, U4TH: N,N'-(2,4-Trimethylhexamethylene)bis[2-(aminocarboxy)propane-1,3-diol]tetramethacrylate
[1] Viscosity of a polymerizable monomer (weighted average viscosity) is shown.

TABLE 2

| Components of Curable Composition for Dental Use | | Comparative Examples | | | | | | | | |
|---|---|---|---|---|---|---|---|---|---|---|
| | | 1 | 2 | 3 | 4 | 5 | 6 | 7 | 8 | 9 |
| Inorganic Particles | a-1 | 99 | 75 | — | 94 | 100 | — | — | 50 | — |
| | a-2 | — | — | 94 | — | — | — | — | 50 | — |
| | a-3 | — | — | — | — | — | — | — | — | — |
| | a-4 | — | — | — | — | — | — | — | — | — |
| | a-5 | — | — | — | — | — | — | — | — | — |
| | a-6 | — | — | — | — | — | — | — | — | — |
| | a-7 | — | — | — | — | — | — | — | — | — |
| | a-8 | — | — | — | — | — | — | — | — | — |
| | a-9 | — | — | — | — | — | — | 94 | — | — |
| | b-1 | — | — | — | 6 | — | — | — | — | 50 |
| | b-2 | 1 | 25 | 6 | — | — | 100 | 6 | — | 50 |
| | b-3 | — | — | — | — | — | — | — | — | — |
| | b-4 | — | — | — | — | — | — | — | — | — |
| Polymerizable Monomer Composition | D2.6E | 18.75 | 18.75 | 18.75 | 18.75 | 18.75 | 18.75 | 18.75 | 18.75 | 18.75 |
| | Bis-GMA | — | — | — | — | — | — | — | — | — |
| | 3G | 6.25 | 6.25 | 6.25 | 6.25 | 6.25 | 6.25 | 6.25 | 6.25 | 6.25 |
| | DD | — | — | — | — | — | — | — | — | — |
| | U4TH | — | — | — | — | — | — | — | — | — |
| | Viscosity (mPa·s)[1] | 54 | 54 | 54 | 54 | 54 | 54 | 54 | 54 | 54 |
| Physical Properties | | | | | | | | | | |
| Forming Property | | 6 | 1 | 1 | 6 | 6 | n.t.[2] | 3 | 6 | n.t.[2] |
| Consistency (mm) | | 45 | 15 | 20 | 47 | 50 | n.t. | 35 | 45 | n.t. |
| Flexural Strength (MPa) | | 160 | 100 | 154 | 138 | 136 | n.t. | 125 | 155 | n.t. |
| Viscosity of Composition (Pa·s) | | 15 | — | 900 | 6 | 4 | — | 135 | 8 | — |

\* The amount of the raw materials of the composition used is expressed by parts by weight.
\* Polymerizable monomer: D2.6E: 2,2-Bis[4-(meth)acryloyloxypolyethoxyphenyl]propane, Bis-GMA: 2,2-bis[4-[3-(meth)acryloyloxy-2-hydroxypropoxy]phenyl]propane, 3G: Triethylene glycol di(meth)acrylate, DD: 1,10-decanediol di(meth)acrylate, U4TH: N,N'-(2,2,4-Trimethylhexamethylene)bis[2-(aminocarboxy)propane-1,3-diol]tetramethacrylate
[1] Viscosity of a polymerizable monomer (weighted average viscosity) is shown.
[2] Not tested.

It can be seen from the above results that the compositions for dental use of Examples have more favorable forming property and consistency, and more excellent flexural strength, as compared to those of the compositions for dental use of Comparative Examples. Among them, from the comparison of Examples 1, 9, and 10, the case where inorganic particles treated with a silane coupling agent having an alkyl chain of 11 are used, the hydrophobic balance of the surface of the inorganic particles is most favorable, so that a composition also having a sufficient strength, while having an appropriate viscosity is obtained. In addition, it can be seen from the comparison of Examples 1, 15, and 16 that the larger the particle size of the inorganic particles having large particle sizes, the smaller the specific surface area, so that the viscosity is lowered and the strength is increased. It can be seen from the comparison of Examples 1 and 4 to 8 that a composition having an appropriate viscosity and strength is obtained by using the two kinds of the inorganic particles as defined in the present invention, regardless of the viscosity of the polymerizable monomer used. On the other hand, from the results of Comparative Example 3, when the inorganic particles having small particle sizes treated with a silane coupling agent having a long alkyl chain are used, there are hardly any effects of providing viscosity, so that a composition having a desired viscosity could not be obtained. From the results of Comparative Example 4, when the inorganic particles having large particle sizes treated with a silane coupling agent having a short alkyl chain are used, the hydrophobic treatment of the surface of the inorganic particles is insufficient, so that the viscosity is presumably increased. From the results of Comparative Examples 8 and 9, even when silane coupling agents having different alkyl chain lengths are used in the treatment of inorganic particles having the same particle size, the effects of the present invention are not found, so that it can be seen that a combination of particle sizes of the particles treated with the silane coupling agents is important. Also, regarding the inorganic particles having large particle sizes, it can be seen from the results of Comparative Example 7 that a sufficient effect is not obtained in a case where the shapes of the inorganic particles are spherical. It is suggested from these findings that compositions having an appropriate viscosity and strength can be obtained by a combined use of the inorganic particles having large particle sizes that are treated with a silane coupling agent having a long alkyl chain, and have irregular shapes, with the inorganic particles having small particle sizes that are treated with a silane coupling agent having a short alkyl chain.

Test Example 4

Measurement of Dynamic Viscoelasticity

Storage modulus (G') and loss modulus (G") were measured for the paste-like composite resins for dental use, prepared in Examples 1, 3 to 6, and 16 and Comparative Examples 1, 3, 5, 7, and 8 under the measurement conditions given below, and a time period during which tan δ [(G")/(G')] satisfies 1 or less, and the value of tan δ after 70 seconds from the beginning of the measurement were calculated, respectively. The results are shown in Table 3.

[Measurement Conditions]
Apparatus: rheometer (AR2000, manufactured by TA Instruments)
Jig: 20 mm, a parallel plate made of aluminum
Sample Stand: stainless steel
Measurement Temperature: 37° C.
Gap: 500 μm
Loading method: A 100% strain is applied at a frequency of 1 Hz to a sample to be measured for 1 minute, and subsequently a 1% strain is applied at a frequency of 1 Hz (a time point at which the application of a 1% strain is started is defined as the beginning of the measurement).

TABLE 3

| Physical Properties | Examples | | | | | |
|---|---|---|---|---|---|---|
| | 1 | 3 | 4 | 5 | 6 | 16 |
| Time period during which tan δ satisfies 1 or less (sec) | 16.8 | 14.5 | 32.6 | 20.5 | 10.7 | 58.5 |
| Value of tan δ after 70 sec | 0.90 | 0.80 | 0.85 | 0.95 | 0.80 | 0.90 |

| Physical Properties | Comparative Examples | | | | |
|---|---|---|---|---|---|
| | 1 | 3 | 5 | 7 | 8 |
| Time period during which tan δ satisfies 1 or less (sec) | * | * | * | ** | * |
| Value of tan δ after 70 sec | 1.3 | 2.5 | 1.5 | 0.5 | 2.3 |

*: tan δ does not satisfy 1 or less within the measurement time (5 minutes).
**: tan δ from the beginning of the measurement is 0 or less.

From the results of Table 3, when the compositions for dental use of Examples 1, 3 to 6, and 16 are compared with Comparative Examples 1, 3, 5, 7, and 8, the compositions of Examples have a shorter time period to satisfy tan δ [(G")/(G')] of 1 or less, so that the time period to which the composition is in a state that begins to show that the property of the elastic member is stronger than the property of the viscosity member is clearly shorter. In addition, it can be seen that even in the value for tan δ after 70 seconds from the beginning of the measurement, the property of the elastic member is strongly exhibited than the property of the elastic member. Therefore, the compositions of these examples can have appropriately low viscosity and forming property because the recovery of the property of the elastic member is fast even after being strained, thereby making it possible to shorten the treatment time. Further, the composition can be suitably used for a direct filling operation to teeth in the treatment because its excellent handling property.

INDUSTRIAL APPLICABILITY

The curable composition for dental use of the present invention can be suitably used as a material capable of substituting a part or all of a natural tooth in the field of dental therapy.

The invention claimed is:
1. A curable composition for dental use, comprising
a polymerizable monomer,
inorganic particles (A) having irregular shapes and an average particle size of from 1.0 to 5.0 μm, wherein the inorganic particles (A) are surface-treated with a silane coupling agent (a) represented by the formula (I):

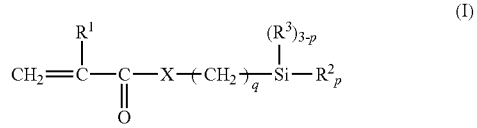

wherein $R^1$ is a hydrogen atom or a methyl group, $R^2$ is a hydrolyzable group, $R^3$ is a hydrocarbon group having 1 to 6 carbon atoms, X is an oxygen or sulfur atom, p is 2 or 3, and q is an integer of from 8 to 13, and
inorganic particles (B) having irregular shapes and/or spherical or nearly spherical shapes, and an average particle size of from 0.01 to 0.10 μm, wherein the inorganic particles (B) are surface-treated with a silane coupling agent (b) represented in the same manner as in the silane coupling agent (a) except that q in the formula (I) is an integer of from 1 to 6,
wherein the inorganic particles (A) and the inorganic particles (B) are contained in amounts of from 85 to 98% by weight and from 2 to 15% by weight, respectively, of the entire amount of the inorganic particles.

2. The curable composition for dental use according to claim 1, wherein the polymerizable monomer has a viscosity at 40° C. of from 20 to 400 mPa·s.

3. The curable composition for dental use according to claim 1 or 2, wherein the polymerizable monomer is contained in a total amount of from 12 to 30 parts by weight, based on 100 parts by weight of the entire amount of inorganic particles.

4. The curable composition for dental use according to claim 1, wherein the polymerizable monomer is at least one member selected from the group consisting of a polymerizable monomer (A) having an aromatic ring without having any hydroxyl groups, a polymerizable monomer (B) having an aromatic ring and a hydroxyl group, and a polymerizable monomer (C) without having any aromatic rings and any hydroxyl groups.

5. The curable composition for dental use according to claim 1, wherein a time period during which tan δ of storage modulus (G') and loss modulus (G"), i.e. tan δ [(G")/(G')], satisfies 1 or less, after application of a 100% strain at a frequency of 1 Hz for one minute and subsequent application of a 1% strain at a frequency of 1 Hz, is from 5 to 60 seconds, wherein a time point at which the application of the 1% strain is started is defined as the beginning of measurement.

6. The curable composition for dental use according to claim 5, wherein tan δ of storage modulus (G') and loss modulus (G"), i.e. tan δ [(G")/(G')], is from 0.5 to 1.0 after 70 seconds from the beginning of measurement.

7. A direct filling restorative material comprising the curable composition for dental use as defined in claim 1.

* * * * *